(12) United States Patent
Leu et al.

(10) Patent No.: US 7,747,418 B2
(45) Date of Patent: Jun. 29, 2010

(54) COMPUTER AIDED DENTAL BAR DESIGN

(76) Inventors: Ming C. Leu, 10517 Pine Lake Dr., Rolla, MO (US) 65401; Amit Gawate, 3701 Parkview La., Apt. 8B, Irvine, CA (US) 92612

( * ) Notice: Subject to any disclaimer, the term of this patent is extended or adjusted under 35 U.S.C. 154(b) by 802 days.

(21) Appl. No.: 11/636,295

(22) Filed: Dec. 8, 2006

(65) Prior Publication Data
US 2007/0134625 A1    Jun. 14, 2007

Related U.S. Application Data

(60) Provisional application No. 60/748,787, filed on Dec. 9, 2005.

(51) Int. Cl.
*G06G 7/48* (2006.01)
(52) U.S. Cl. .............. 703/6; 703/7; 345/418; 433/24; 433/173; 433/128
(58) Field of Classification Search ............... 433/24, 433/218; 703/11; 382/154; 705/3
See application file for complete search history.

(56) References Cited

U.S. PATENT DOCUMENTS 6,948,931 B2 * 9/2005 Chishti et al. ................ 433/24
7,123,767 B2 * 10/2006 Jones et al. .................. 382/154
7,156,655 B2 * 1/2007 Sachdeva et al. ............. 433/24
2004/0017369 A1 * 1/2004 Hultgren et al. .............. 345/423
2005/0010450 A1 * 1/2005 Hultgren et al. ............... 705/3
2005/0170309 A1 * 8/2005 Raby et al. .................... 433/24
2006/0095242 A1 * 5/2006 Marshall ...................... 703/11
2006/0115795 A1 * 6/2006 Marshall et al. ............. 433/218

OTHER PUBLICATIONS

M. Gopi and Shankar Krishnan A Fast and Efficient Projection-Based Approach for Surface Reconstruction Proceedings of the XV Brazilian Symposium on Computer Graphics and Image Processing, SIBGRAPHI'02, 1530-1834/02, 2003 IEEE.*

* cited by examiner

*Primary Examiner*—Kamini S Shah
*Assistant Examiner*—Cuong V Luu
(74) *Attorney, Agent, or Firm*—C. John Brannon; Brannon & Sowers PC

(57) ABSTRACT

The invention relates to a computer-aided process of dental bar design for the purpose of fabricating removable implant-based dental restorations. The aim of the invention is to improve and automate the present dental restoration design process, which is very labor intensive and requires a lot of artistic work on the part of a dentist. The invention includes the developments of several algorithms and their integration into a computer-aided system to process the gingival and related data scanned from a patient's mouth and output a CAD model for fabricating the actual dental bar. Software has been developed to implement the inventive process.

1 Claim, 7 Drawing Sheets

Direction of viewing line (Z-axis) →

Case 1

Case 2

Case 3

Case 4

ZCN – Near Z value of the connecting bar model
ZCF – Far Z value of connecting bar model
ZGN – Near Z value of gingiva model
ZGF – Far Z value of gingiva model Direction of viewing line (Z-axis)

Case 1

Case 2

Case 3

Case 4

ZBN – Near Z value of bar-cylinder model
ZBF – Far Z value of bar-cylinder model
ZMN – Near Z value of modified connecting bar model
ZMF – Far Z value of modified connecting bar model

COMPUTER AIDED DENTAL BAR DESIGN

This application claims the benefit of the U.S. Provisional Application No. 60/748,787, filed on Dec. 9, 2005.

FIELD OF THE INVENTION

The present invention relates to a method of designing a dental bar in a dental restoration system. More particularly, the present invention directs to a computer-aided process of dental-bar design for the purpose of fabricating removable implant-based dental restorations.

BACKGROUND OF THE INVENTION

The dental bar is an important piece in the implant-based dental restorations for partially or fully edentulous patients. Implant-based dental restorations have many advantages over standard removable dental restorations since the implants can prevent the loss of jawbones, especially in older patients, help to restore facial features, and enable the patients to get firm bites. A critical step in dental restoration is the fabrication of the dental bar on which the ceramic denture sits. A dental bar is patient-specific, i.e., a particular dental bar is outfitted for a particular patient as each patient's jaw is unique, and needs to be fitting firmly in a patient's mouth and confirming to the shape of the patient's gingival surface. Thus, the design of a dental bar is a crucial step in the fabrication of the dental bar and eventually success of the dental restoration.

Traditionally, designing of a dental bar has been done manually by a dentist, which is a lengthy and labor intensive process and requires high levels of artistic work on the part of the dentist. There have been attempts to develop methods and systems towards automated design and fabrication of dental bars, however, with very limited successes. Currently, the commercially available "automated" dental restoration systems are only capable of making restorations for single tooth, not for edentulous patients requiring multiple teeth restorations.

For example, CEREC® is a commercially available CAD/CAM system for design and fabrication of ceramic dental restorations (http://www.cereconline.com). The system consists of a data acquisition device (infrared camera), a milling machine unit, and a software module that generates the missing part of a patient's tooth. A dentist can use the system for crowns, fillings, and single-tooth restorations.

Procera® technology is another commercially available CAD/CAM process that involves computer generated copings to provide precision fit within the acceptable level according to the standards of American Dental Association (http://www.nobelbiocare.com). Prior to this technology all-ceramic restorations had to be bonded into place using resin cements, due to lack of strength and marginal integrity of the restorations. Crown restorations for single tooth produced by Procera® have been shown to be within the clinically accepted range for marginal opening gap dimensions.

The inventors' lab previously attempted to develop an automated process for dental bar design with limited success. The previous attempt is documented in Mr. Po-Wen Yang's thesis tilted "Feasibility Study of 3-D Cylinder Data Fitting on the Bar-retained Removeable Overdenture Design."

Therefore, it is desirable to develop a novel, automated method and system to design a dental bar for dental restorations.

SUMMARY OF THE INVENTION

The present invention provides a novel method for automated dental-bar design for implant-based dental restorations. The inventive method takes a set of digital scan data representing the patient's gingival surface and generates the geometric model of a dental bar ready for fabrication of an actual dental bar by rapid prototyping (i.e. solid freeform fabrication) or numerically controlled (NC) machining techniques. In the inventive process, a first set of data points representing the gingival surface of a patient with pre-implanted healing abutments is retrieved. A geometric model for the patient's gingiva ("Gingiva Model") is developed from the first set of data. A second set of data points representing positions and orientations of healing abutments is computed based on the first set of data points. A geometric model for a dental-bar connector ("Connector Model") is developed from the second set of data. A geometric model for the dental-bar cylinders ("Cylinder Model") is also developed from the second set of data. Then, the aforesaid models, the Gingiva Model, the Connector Model, and the Cylinder Model, are overlaid and processed to construct a geometric model for the dental bar ("Dental-Bar Model"), based on which the actual dental bar can be fabricated.

In a preferred embodiment, to construct the Gingiva Model, the first set of data points is converted via an inventive Gingival Surface Reconstruction Algorithm. Prior to the constructions of the Connector Model and the Cylinder Model, the first set of data points is selected to obtain a set of point cloud representing the contours and shapes of the healing abutments, and the set of point cloud is sorted to derive a second set of data points representing the positions and orientations of the healing abutments. Then the Cylinder Model and the Connector Model are constructed by converting the second set of data points via an inventive Bar-Cylinder Generation Algorithm and an inventive Connecting Bar Generation Algorithm, respectively.

To create the Dental-Bar Model, the three aforesaid models are overlaid and processed using Boolean operations via an inventive Dental-Bar Shaping Algorithm. Specifically, the top or bottom surface (depends on whether an upper or lower gingival surface is employed) of the Connector Model is first modified by the gingival surface of the Gingiva Model. Then, the modified Connector Model is combined with the Cylinder Model to yield the Dental-Bar Model.

DETAILED DESCRIPTION OF THE INVENTION

Figure 1:
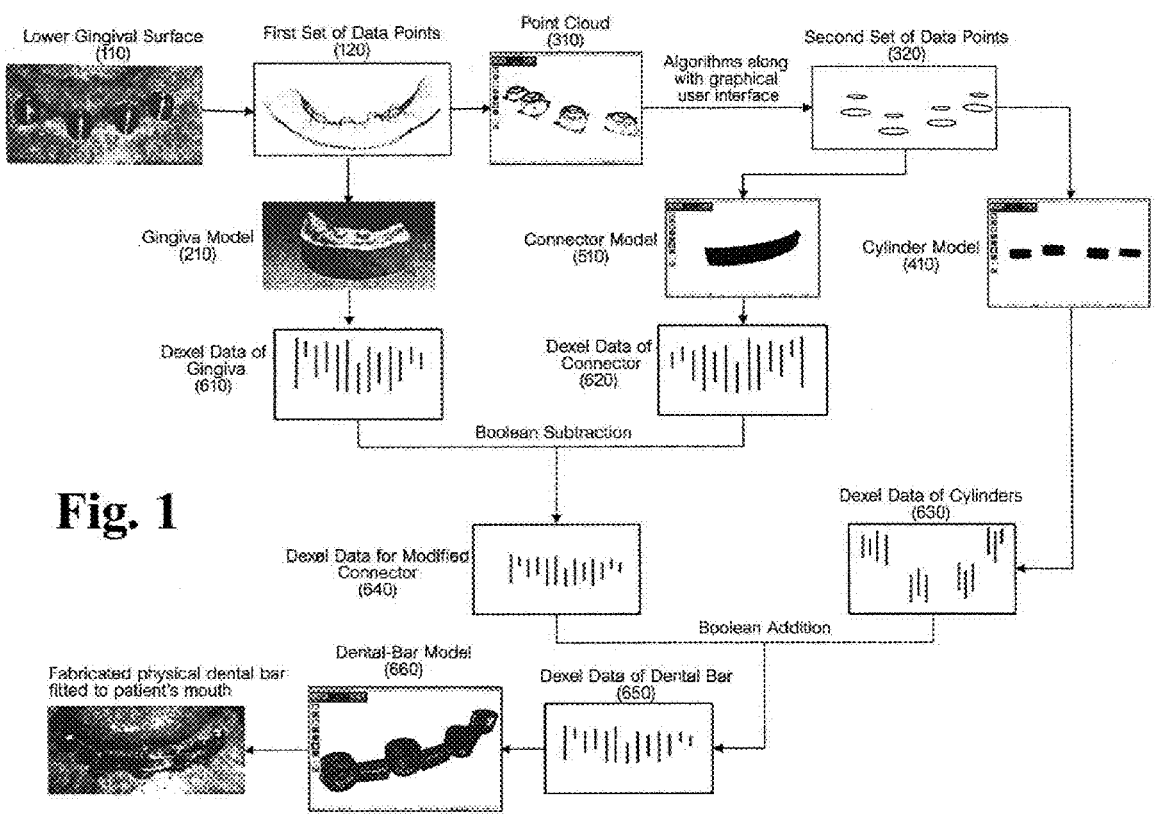
FIG. 1 is a detailed flowchart of the inventive dental bar design process with preferred embodiment.

The present invention provides an automated method of dental-bar design for implant-based dental restorations, which can be used for partially or completely edentulous patients. The inventive method takes a set of digital scan data that represents a patient's gingival surface (of either the upper or lower jaw) and designs a patient-specific dental bar in the form of a triangular-mesh model, which can then be used to fabricate a physical dental bar by computer-aided manufacturing. Specifically, the inventive method to design a dental bar for a patient comprises the following steps:

a. Retrieving a first set of data points representing the patient's gingival surface (upper or lower) with pre-implanted healing abutments (100);
 b. Constructing a geometric model for the gingiva (Gingiva Model) from the first set of data points (200);
 c. Computing a second set of data points representing positions and orientations of the abutments (and hence the implants) from the first set of data points (300);
 d. Constructing a geometric model representing cylinders (Cylinder Model) from the second set of data points (400);
 e. Constructing a geometric model for a connecting bar (Connector Model) from the second set of data points (500); and
 f. Constructing a geometric model for the dental bar (Dental-Bar Model) by overlaying and processing the Connector Model, the Cylinder Model, and the Gingiva Model (600).

In a preferred embodiment, the aforesaid Gingiva Model constructing step (200) is achieved via the inventive Gingival Surface Reconstruction Algorithm; the Cylinder Model constructing step (400) via the inventive Bar-Cylinder Generation Algorithm; the Connector Model constructing step (500) via the inventive Connecting Bar Generation Algorithm; the Dental-Bar Model constructing step (600) via the inventive Dental Bar Shaping Algorithm. The detailed process is illustrated by FIG. 1, where a patient's lower gingival surface (110) is depicted with four healing abutments.

In Step 100, the first set of data points (120) representing the geometric information of the gingival surface and the surface geometry of the healing abutments, can be retrieved in two ways, directly or indirectly. In the direct method, a small infrared or laser camera or some other suitable scanning device is placed in the patient's mouth and scans the gingival surface (110). In the indirect method (not shown), an impression of patient's mouth is taken, and a stone model is constructed. The stone model is then scanned using a contact or non-contact type digitizer.

Figure 2A:
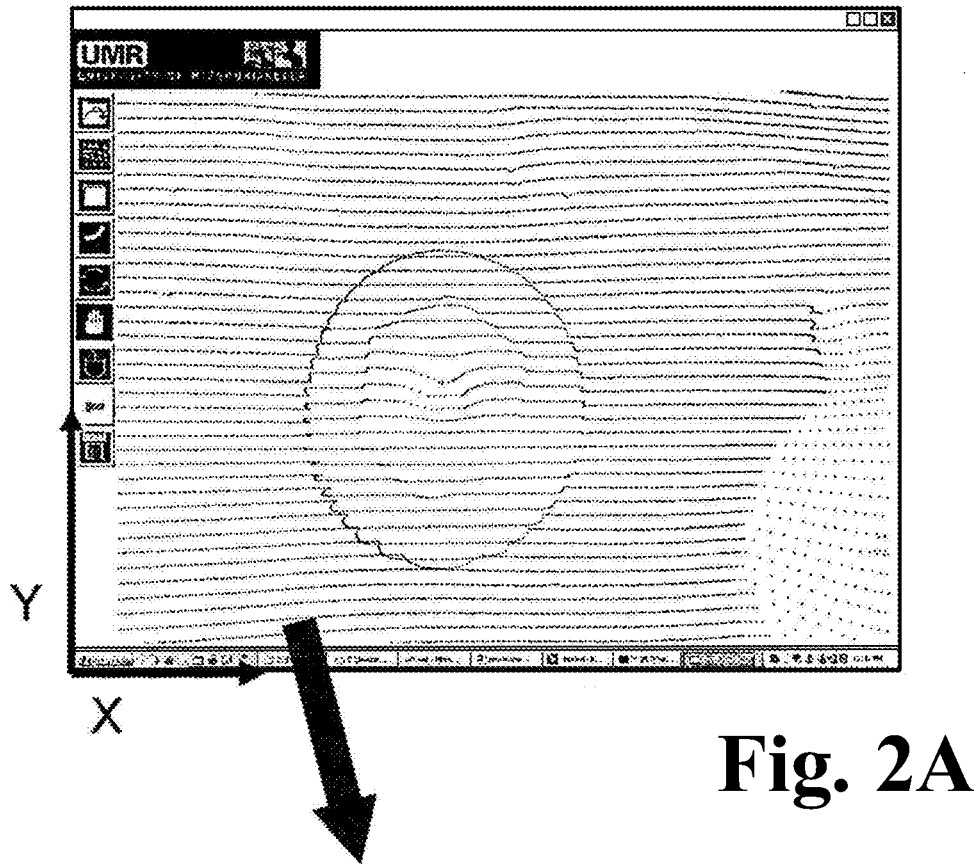
FIG. 2 illustrates the first set of data points on scan lines and the Gingival Surface Reconstruction Algorithm.
Figure 2B:
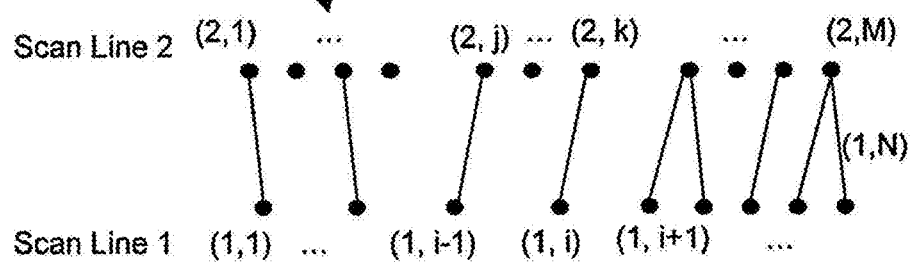
Figure 2C:
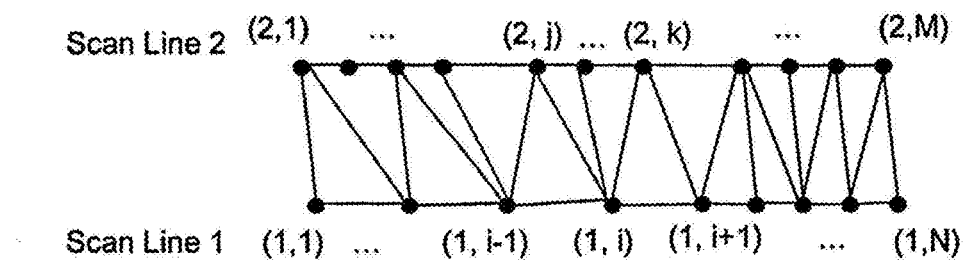

In Step 200, a geometric model of the patient's gingiva, the "Gingiva Model," shown as 210 in FIG. 1, is constructed from the first set of data points (120) via the Gingival Surface Reconstruction Algorithm implemented in computer software. FIG. 2(*a*) illustrates the first set of data points taken from scanning the gingival surface of a patient's mouth. FIGS. 2(*b*) and 2(*c*) illustrate how the first set of data points is arranged along the scan lines and connected according to the inventive algorithm.

Figure 3:
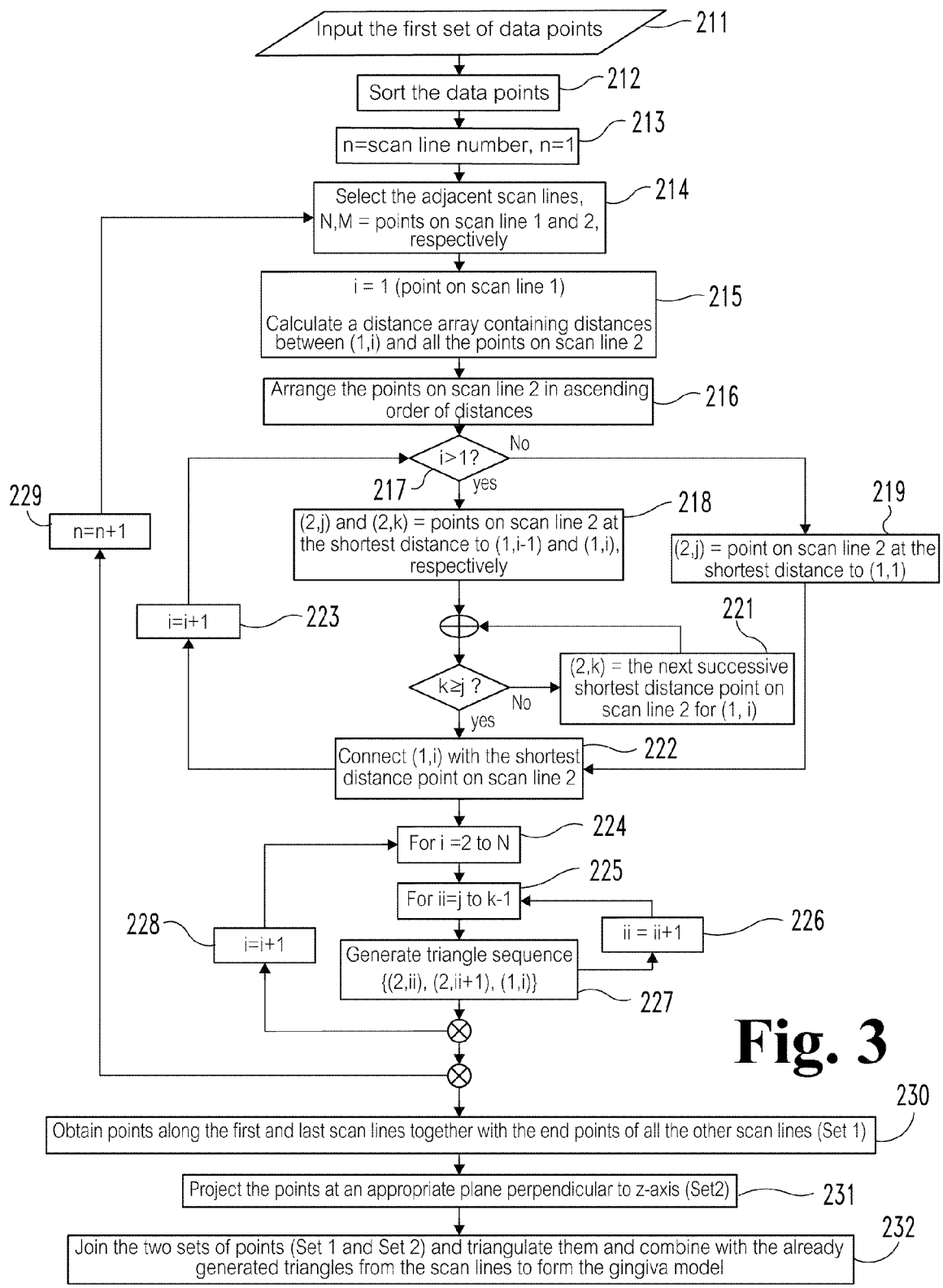
FIG. 3 is a flowchart depicting the Gingival Surface Reconstruction Algorithm.

FIG. 3 illustrates the steps of the inventive Gingival Surface Reconstruction Algorithm, which consist of the following steps:

i. Arrange the data in order of scan lines, as shown in FIG. 2 and Boxes 211-213 of FIG. 3.
 ii. Two adjacent scan lines closest to the X-axis are selected first. The scan line having fewer points of the two scan lines is called "Scan Line 1". The other scan line with more points is called "Scan Line 2". Let the number of points on scan line 1 be N and the number of points on Scan line 2 be M (Box 214 of FIG. 3).
 iii. Calculate the distances of the first point on Scan Line 1 with all M points on Scan Line 2 (Box 215 of FIG. 3).
 iv. Arrange the points on Scan Line 2 in the order of increasing distance from the first point on Scan Line 1 (Box 216 of FIG. 3). Connect the first point on Scan Line 1 with the point at the shortest distance on Scan Line 2 (Boxes 217-222 of FIG. 3).
 v. Repeat steps (iii) and (iv) to determine the shortest distance for the remaining (N−1) points on scan line 1 (Boxes 223). For every point (1, i) on scan line 1, starting from i=2 (the second point), let the point at the shortest distance on scan line 2 be (2, k). Also let (2, j) be the point on scan line 2 at the shortest distance from point (1, i−1). If k<j, select the point on scan line 2 at the next shortest distance from (1, i) and repeat the process until the condition k≧j is satisfied.
 vi. Connect point (1, i) with point (2, k), for i=2, . . . N. This is illustrated in FIG. 2(*b*).
 vii. For every point (1, i) on scan line 1, starting from the second point i.e. i=2, connect it with the points between (2, j) and (2, k) in the form of triangular fan mesh. Thus, the triangle sequence obtained for the points between (2, j) and (2, k) are {(1, i), (2,j), (2,j+1)}, {(1, i), (2, j+1), (2, j+2)}, . . . , {(1, i), (2, k−1), (2,k)} (Boxes 224-227 of FIG. 3). Repeat the process until all the points on scan line 2 are connected with all the points on scan line 1 in the form of triangular mesh (Box 228 of FIG. 3). The triangular mesh after all the points are connected is illustrated in FIG. 2(*c*).
 viii. Repeat steps (ii) to (vii) for all the other scan lines until all the points on the successive scan lines are connected by triangles to form a triangular mesh (Box 229 of FIG. 3).
 ix. Make the projection of Point Set 1, which consists of the points along the first and last scan lines together with the end points of all the other scan lines, to a plane Z=k, which is an appropriate plane parallel to the XY-plane. The projection points collectively are termed Point Set 2. Triangulate the points in Point Set 1 and Point Set 2 and combine the generated triangles with the aforesaid triangles (Boxes 230-232 of FIG. 3), which are generated from the points on the scan lines, to form a triangular mesh of the top, side and bottom of the Gingiva Model.

In Step 300, the first set of data points (120) obtained in Step 100 is filtered/selected to obtain a set of point cloud (310) representing the geometric information of the healing abutments. A Visual Interface is provided to a user during the selection of the set of point cloud (310). The set of point cloud (310) is then filtered again to get a second set of data points (320) representing the top edge of each healing abutment. The second set of data points (320), which is around circles in 3-D space, is used to determine the best fit of circles.

Figure 4A:
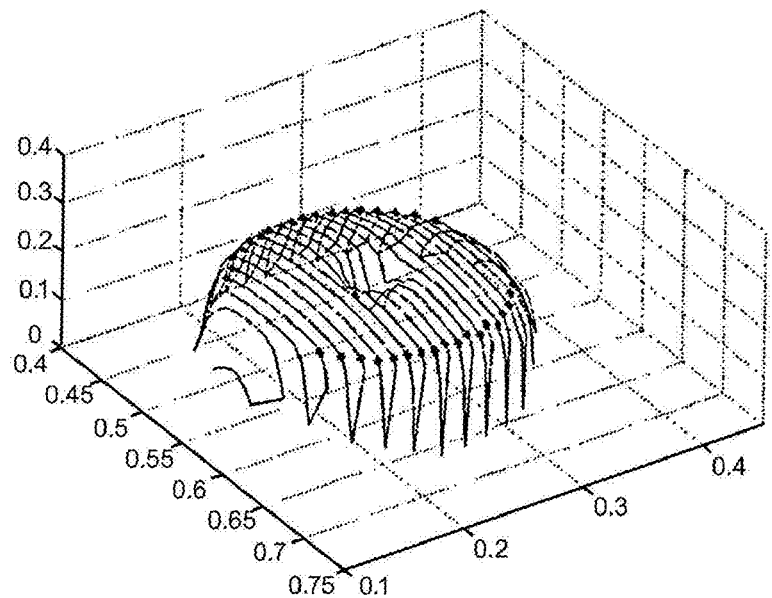
FIG. 4 shows the points with sudden slope changes around the top edge of a healing abutment and a circle fitted through these points.

A Bar-Cylinder Generation Algorithm is used to filter out the points around the top edge of a healing abutment, to fit a circle through these points, and to generate bar cylinders for the Cylinder Model. The Bar-Cylinder Generation Algorithm comprises the following steps:

i. The points on each scan line are selected from the first set of data points and they are arranged in increasing order of X-coordinate.
ii. These points are sorted using the criterion that the slope of two successive points on the cylinder wall, which is nearly vertical, is very large.
iii. The slope of two successive points is calculated using the equation: Slope=(Z2−Z1)/(X2−X1), where Z1 and Z2 are the Z-coordinates of the two consecutive data points, and X1 and X2 are the X-coordinates of the two consecutive data points. The slope of the two consecutive points is stored in an array, and then the stored slopes are retrieved and compared to identify a sudden change in slope.
iv. The point with a sudden slope change is selected for each scan line. When the slope of two consecutive points changes from a very low to a very high value, or from a very high to a very low value, the point where the slope changes drastically is selected.
v. The same procedure in step (iv) is repeated for all the other scan lines. FIG. 4(a) illustrates the points obtained. The asterisks indicate the points on the circle.
vi. The selected points are used as input to fit a circle in 3-D space. The axis of the circle indicates the position and orientation of each healing abutment. To find the orientation of the circle, a Singular Value Decomposition Algorithm is used (refer to "Singular Value Decomposition and Least Square Solutions," G. H. Golub et al., SIAM Journal of Scientific and Statistical Computing, Vol. 4, pp. 410-417, 1981). This algorithm decomposes an overdetermined system of equations into eigen values and eigen vectors. The eigen vectors obtained by the SVD algorithm are the directional cosines of the normal to the plane of the circle that has best fit to the selected points.
vii. To find the plane that has the best fit through all the points, use the equation of the best-fit plane given by $$a(x-x_o)+b(y-y_o)+c(z-z_o)=0$$

where $(x_o, y_o, z_o)$ represents the x-y-z coordinates of a point lying on the plane and (a, b, c) represents the direction cosines of the normal to the best-fit plane that passes through $(x_o, y_o, z_o)$.

The shortest distance of a point $(x_i, y_i, z_i)$ to the best fit plane passing through the point $(x_o, y_o, z_o)$ and having directional cosines (a, b, c) is given by $$d_i = |a(x_i-x_o)+b(y_i-y_o)+c(z_i-z_o)|$$

To pass the best-fit plane through the data points, the sum of the squares of the shortest distance $d_i$ between the given points and the best-fit plane is minimized. The best-fit plane passes through the centroid $(x_c, y_c, z_c)$ of the given points and minimizes the sum of the squares of the distance $d_i$ between the plane and the given points.

Figure 4B:
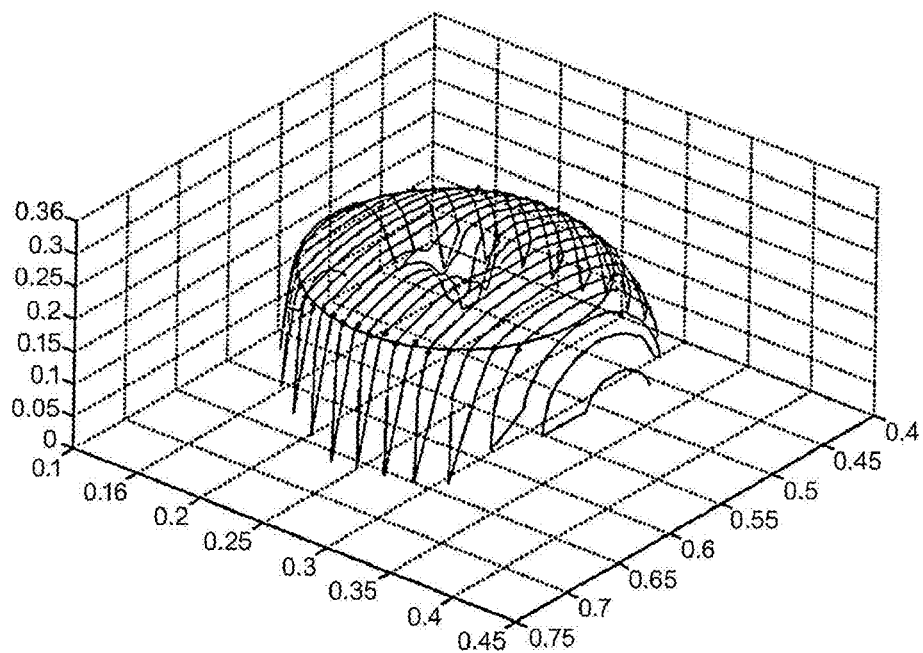

The directional cosines of the normals to the best-fit plane are found by the Singular Value Decomposition (SVD) of the following matrix $$A = \begin{bmatrix} x_1 - x_c & y_1 - y_c & z_1 - z_c \\ x_2 - x_c & y_2 - y_c & z_2 - z_c \\ \vdots & \vdots & \vdots \\ x_n - x_c & y_n - y_c & z_n - z_c \end{bmatrix}$$

where $(x_1, y_1, z_1), \ldots, (x_n, y_n, z_n)$=points from which the best-fit plane is sought. Applying the SVD to matrix A gives:

$$[R, S, V] = SVD(A)$$

such that $$R * S * V = A$$

$$S = \begin{bmatrix} \lambda_1 & 0 & 0 \\ 0 & \lambda_2 & 0 \\ 0 & 0 & \lambda_3 \end{bmatrix}$$

$$V = \begin{bmatrix} a_{\lambda 1} & a_{\lambda 2} & a_{\lambda 3} \\ b_{\lambda 1} & b_{\lambda 2} & b_{\lambda 13} \\ c_{\lambda 1} & c_{\lambda 2} & c_{\lambda 3} \end{bmatrix}$$

where S is the diagonal matrix (n×n), containing the eigen values $(\lambda_i)$ in the diagonal components, and V is the orthogonal matrix containing eigen vectors of the matrix A The directional cosines (a, b, c) of the best-fit plane is the column vector of matrix V which has the maximum corresponding eigen value in the diagonal matrix 'S'. The next step is to transform the plane and hence its associated points such that the best-fit plane lies on the principal XY-plane. The transformation used for this is:

$$U = \begin{bmatrix} c_2 & 0 & s_2 \\ 0 & 1 & 0 \\ -s_2 & 0 & c_2 \end{bmatrix} \begin{bmatrix} 1 & 0 & 0 \\ 0 & c_1 & s_1 \\ 0 & -s_1 & c_1 \end{bmatrix}$$

where $$c_1 = c / \sqrt{b^2 + c^2}$$

$$s_1 = -b / \sqrt{b^2 + c^2}$$

$$c_2 = (cc_1 - bs_1) / \sqrt{a^2 + (cc_1 - bs_1)^2}$$

$$s_2 = -a / \sqrt{a^2 + (cc_1 - bs_1)^2}$$

viii. Fit the data points with the best-fit circle to calculate the center and the radius of the circle. The least square method is used for fitting these points with a circle. FIG. 4(b) illustrates the sorted points on the top surface of the healing abutment and the circle that is fitted through them.
ix. Obtain a set of points on the circumference of the circle using the center and radius of the best-fit circle.
x. Compute a second set of points by projecting the points of the circle on the XY-plane to a new plane Z=h, where 'h' is the height of the bar-cylinder.
xi. Back-transform the two sets of points obtained in steps (ix) and (x) to the original coordinate system. This is achieved by using the transformation matrix $U^T$, where U is the matrix obtained in step (vii) and the superscript T represents the transpose of a matrix.
xii. Repeat steps (vi) to (xi) to generate the sets of points for all the other bar cylinders.
xiii. Determine the sequence to connect the transformed points to form triangular meshes for the bar cylinders.

The triangular mesh of each bar cylinder in the Cylinder Model constructed in Step 400 as detailed above needs to be connected together by a connecting bar (Connector). The Connecting Bar Generation Algorithm is used in Step 500 to generate the Connector in a triangular mesh model (Connector Model) for connecting these cylinders.

Figure 5:
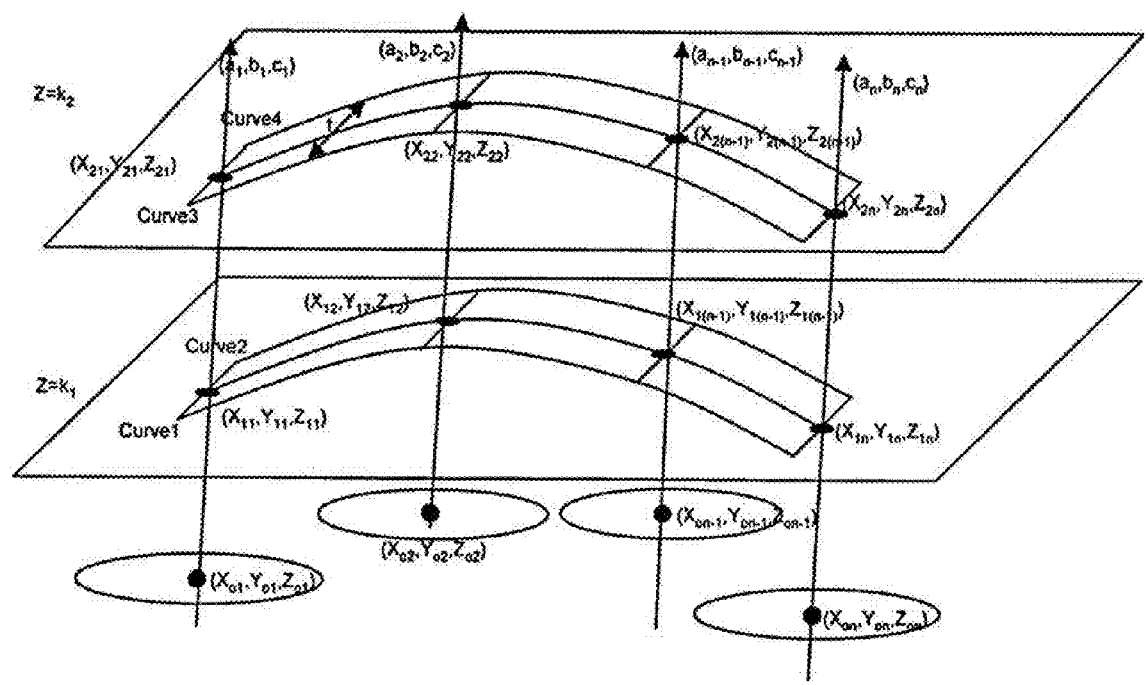
FIG. 5 provides an illustration for the Connecting Bar Generation Algorithm

The connecting bar generation algorithm comprises the following steps (see FIG. 5 for illustration):

i. Obtain the equations of the axes of the bar cylinders in 3-D space using the positions and directional cosines of the best-fit circles. Assuming the axis of the first cylinder passes through $(x_{o1}, y_{o1}, z_{o1})$ and has directional cosines $a_1$, $b_1$, and $c_1$, then the equation of the axis of the first cylinder in 3-D space is given by $$\frac{x - x_{o1}}{a_1} = \frac{y - y_{o1}}{b_1} = \frac{z - z_{o1}}{c_1}$$

ii. Compute the points of intersection of the axis of the first cylinder with planes $Z=k_1$ and $Z=k_2$, which pass through the top face and the bottom face of the connecting bar. Let the points of intersection be $(X_{11}, Y_{11}, Z_{11})$ for plane $Z=k_1$ and $(X_{21}, Y_{21}, Z_{21})$ for plane $Z=k_2$ iii. Compute the points of intersection for the remaining cylinder axes and the two planes $Z=k_1$ and $Z=k_2$. The points of intersection are $(X_{12}, Y_{12}, Z_{12}), \ldots, (X_{1n}, Y_{1n}, Z_{1n})$ for plane $Z=k_1$ and $(X_{22}, Y_{22}, Z_{22}), \ldots, (X_{2n}, Y_{2n}, Z_{2n})$ for plane $Z=k_2$.

iv. Generate a cubic or other spline curve passing through the points on the plane $Z=k_1$ obtained in steps (ii) and (iii).

v. Repeat step (iv) to determine the equation of the curve passing through the points on the plane $Z=k_2$.

vi. The thickness 't' of the connecting bar is used to generate four new curves (two in each of the two planes expressed in terms of discrete points along these curves): Curve1 and Curve2 on the plane $Z=k_1$, and Curve3 and Curve4 on the plane $Z=k_2$.

vii. The discrete points on these four curves are joined in a sequence to generate a connecting bar in the format of triangular mesh.

In Step 600, a Dental-Bar Model is constructed by overlaying the Connector Model, the Cylinder Model, and the Gingiva Model so that the bottom (or top) part of the connecting bar conforms to the patient's lower (or upper) gingival surface with a pre-specified gap. In one embodiment, Step 600 can be achieved in two substeps. First, the Connector Model is modified with the Gingiva Model to yield the Modified Connector Model; then, the Modified Connector Model is combined with the Cylinder Model to yield the Dental-Bar Model.

In the preferred embodiment as shown in FIG. 1, Step 600 is achieved via the inventive Dental Bar Shaping Algorithm. Generally speaking, this inventive algorithm can be divided into four core steps as follows:

First, the algorithm converts the triangular mesh models into dexel data sets using a ray casting based Z-buffer algorithm. As shown in FIG. 1, the triangular mesh Gingiva Model (210) is converted into a set of dexel data for the gingiva (610); the triangular mesh Connector Model (510) is converted into a set of dexel data for the connecting bar (620); and the triangular mesh Cylinder Model (410) is converted into a set of dexel data for the bar cylinder (630).

Second, Boolean subtraction of the set of dexel data for the gingiva (610) is performed on the set of dexel data for the connecting bar (620) to yield a set of dexel data for the modified connecting bar (640).

Third, the set of dexel data for the modified connecting bar (640) is united with the set of dexel data for the bar cylinders (630) via Boolean addition to yield a set of dexel data for the dental bar (650).

Fourth, the set of dexel data for the dental bar (650) is converted back to a triangular mesh model of the dental bar (Dental-Bar Model) (660), which serves as the design model of the dental bar to be fabricated to a physical dental bar for the patient.

Figure 6:
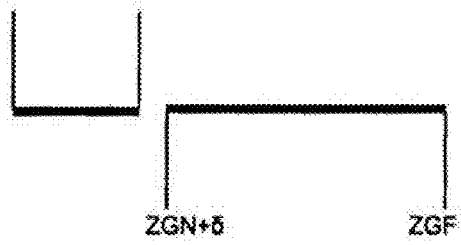
FIG. 6 illustrates the cases existing in performing Boolean subtraction of the dexel data of the Gingiva Model from the dexel data of the Connector Model.
Figure 6:
Figure 6:
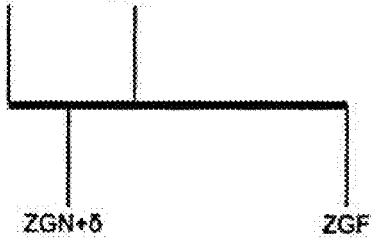
Figure 6:
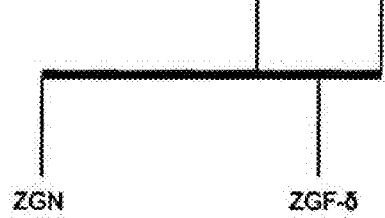

Specifically, the Dental Bar Shaping Algorithm consists of the following particular steps:

i. The Gingiva Model, the Cylinder Model, and the Connector Model are converted into dexel models using the Z-buffer algorithm. The dexel model is obtained by computing the intersections of rays with a solid object of concern. For a given solid object, a set of parallel and equidistant rays are projected and intersected with the object. For each ray the points of intersection with the object are stored in the following manner: Two points defining a line within a solid object make up a dexel. All the dexel data are separated and combined in the form of a linked list. The list is stored in the form of a matrix.

ii. The dexel data of the gingiva in the form of near and far Z values (ZGN and ZGF), of the connecting bar (ZCN and ZCF), and of the bar-cylinders (ZBN and ZBF) are obtained and stored in dexel data groups.

iii. The dexel data obtained for the connecting bar are compared with the dexel data obtained from the patient's gingiva. The algorithm shapes the bottom (or top) profile of the connecting bar by Boolean subtraction of the Gingiva Model from the Connector Model using the dexel data. The dexel data of the coincident rays of both models are compared and depending upon the overlap between the dexel data of the two models, the resultant dexel data is calculated for the Boolean subtraction. The steps for shaping the bottom profile of the final dental bar model for fitting with the patient's gingival surface can be done by reducing the dexel height of the dental bar model as follows (see FIG. 6 for illustration):

a. A small positive value $\delta$, which represents the gap between the dental bar and the patient's gingival surface, is used to modify the dexel data of the Connector Model to provide a gap between the dental bar and the gingival surface. There are four cases that may arise from the comparison between the dexel data of the Connector Model and the dexel data of the Gingiva Model, as shown in the FIG. 6.

b. For cases (1), the two models do not intersect each other. No action is needed. Thus the modified connecting bar model will have the same dexel data as the initial connecting bar model i.e.

ZMN=ZCN

ZMF=ZCF where ZMN is the near Z value of dexel data of the modified connecting bar model, and ZMF is the far Z value of dexel data of the modified connecting bar model.

c. Case (2) exists for the design of a dental bar for the upper jaw. For this case no action is needed and the dexel values of the modified connecting bar are:

ZMN=ZCN

ZMF=ZCF d. In case (3), the dexel data of the two models overlap each other. In this case, the far dexel data of the modified connecting bar is replaced by the near dexel data of the Gingiva Model as follows:

ZMN=ZCN $ZMF=ZGN+\delta$ e. In case (4), the dexel data of the two models overlap each other, with the dexel data of the Gingiva Model coming first in the line of view. This case occurs in designing the dental bar for the upper jaw. In this case, the near dexel data of the final dental bar is replaced by the far dexel data of the Gingiva Model. i.e.

$ZMN=ZGF-\delta$

Figure 7:
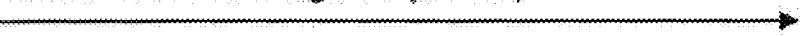
FIG. 7 illustrates the cases existing in performing Boolean addition between the dexel data of the Modified Connecting Bar Model and the dexel data of the Cylinder Model.
Figure 7:
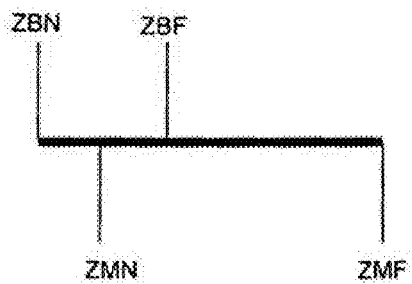
Figure 7:
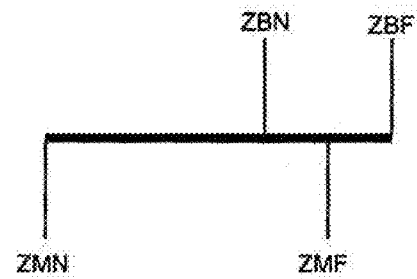
Figure 7:
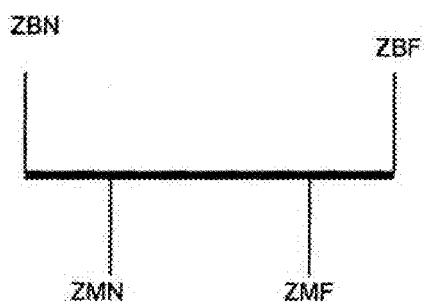
Figure 7:
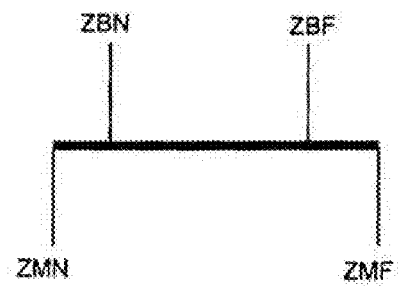

ZMF=ZCF iv. The dexel data of the modified connecting bar (ZMN, ZMF) and the dexel data of the bar-cylinders (ZBN, ZBF) are then compared and Boolean addition performed on these two sets of data. The Boolean addition is done by considering different cases with the following steps (see FIG. 7 for illustration):
  a. Arrange the list of dexel data on the bar-cylinder along each viewing line.
  b. Obtain the ZBN, ZBF and ZMN, ZMF along the viewing line for the bar-cylinder and the modified connecting bar dexel data, where ZBN is the near Z value of the bar-cylinder dexel, ZBF is the far Z value of the bar-cylinder dexel, ZMN is the near Z value of the modified connecting bar dexel, and ZMF is the far Z value of the modified connecting bar dexel.
  c. Compare the dexel data of the modified connecting bar model and the dexel data of the bar-cylinder model and classify them into one of the following four cases, as illustrated in FIG. 7.
  d. Case 1: For the case that the Z values satisfy the condition ZBN>ZMN>ZBF>ZMF, the dexel data after the Boolean addition is

ZDN=ZBN

ZDF=ZMF where ZDN is the near Z value of the final dental bar dexel, and ZDF is the far Z value of the final dental bar dexel.
  e. Case 2: For the case that the Z values satisfy the condition ZMN>ZBN>ZMF>ZBF, the dexel data after the Boolean addition is

ZDN=ZMN

ZDF=ZBF f. Case 3: For the case that the Z values satisfy the condition ZBN>ZMN>ZMF>ZBF, the dexel data after the Boolean addition is

ZDN=ZBN

ZDF=ZBF g. Case 4: For the case that the Z values satisfy the condition ZMN>ZBN>ZBF>ZMF, the dexel data after the Boolean addition is

ZDN=ZMN

ZDF=ZMF v. The obtained dexel data are used to construct the triangular mesh of the boundary surface of the final dental bar model using a surfaced reconstruction algorithm (refer to "Surface Reconstruction from Dexel Data for Virtual Sculpting," X. Peng, W. Zhang, S. Asam and M. C. Leu, Proceedings of ASME International Mechanical Engineering Conference, Anaheim, Calif., Nov. 14-19, 2004). The final dental bar model has its bottom profile conforming to the gingival surface of the patient's lower jaw, or its top profile conforming to the gingival surface of the patient's upper jaw, with a pre-specified gap between the dental bar and the gingival surface to prevent the dental bar from exerting pressure on the gingiva.

More detailed description of the invention can be found in the thesis of an inventor, Amit Gawate, titled "Computer Aided Software Tool for Design of Dental Bar." The thesis is hereby incorporated into the application.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A method for producing a Dental-Bar Model to be fitted on a patient's upper (or lower) gingival surface comprising the steps of
  a) retrieving a first set of data points representing the gingival surface of patient's upper (or lower) with healing abutments;
  b) constructing a triangular mesh model for the patient's gingiva (Gingiva Model) based on the first set of data points;
  c) computing a second set of data points representing positions and orientations of the healing abutments based on the first set of data points;
  d) constructing a triangular mesh model for a dental-bar connector (Connector Model) based on the second set of data points;
  e) constructing a triangular mesh model for the bar cylinders (Cylinder Model) based on the second set of data points;
  f) comparing and overlaying the Gingiva Model, the Connector Model, and the Cylinder Model to construct the Dental-Bar Model, based on which a physical dental bar can be fabricated;
  wherein step f) further comprises:
  f1) converting the triangular mesh Gingiva Model into a set of dexel data for the gingiva;
  f2) the triangular mesh Connector Model into a set of dexel data for the connecting bar;
  f3) converting the triangular mesh Cylinder Model into a set of dexel data for the cylinder;
  f4) subtracting the set of dexel data for the gingival from the set of dexel data for the connecting bar to yield a set of dexel data for a modified connecting bar;
  f5) combining the set of dexel data for the bar cylinders with the set of dexel data for the modified connecting bar to yield a set of Drexel data for the dental bar; and
  f6) converting the set of dexel data for the bar to the triangular mesh model for the dental bar.

* * * * *